US006252393B1

(12) United States Patent
Hedengren

(10) Patent No.: US 6,252,393 B1
(45) Date of Patent: Jun. 26, 2001

(54) SYSTEM AND METHOD FOR NORMALIZING AND CALIBRATING A SENSOR ARRAY

(75) Inventor: Kristina Helena Valborg Hedengren, Schenectady, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/330,108

(22) Filed: Jun. 10, 1999

Related U.S. Application Data
(60) Provisional application No. 60/090,293, filed on Jun. 23, 1998.

(51) Int. Cl.[7] ............................. G01R 35/00; G01N 27/90
(52) U.S. Cl. ............................ 324/202; 324/232; 324/242
(58) Field of Search .................................. 324/202, 227, 324/232, 242, 262; 73/1.86

(56) References Cited

U.S. PATENT DOCUMENTS

| | | | |
|---|---|---|---|
| 3,718,855 | * 2/1973 | Rogel et al. ............................ | 324/202 |
| 4,280,094 | * 7/1981 | Karlsson ................................. | 324/202 |
| 4,418,315 | * 11/1983 | Edwards et al. ........................ | 324/202 |
| 4,425,545 | * 1/1984 | Scalese .................................... | 324/202 |
| 4,963,826 | * 10/1990 | Capobianco et al. ................... | 321/202 |
| 5,182,513 | 1/1993 | Young et al. ........................... | 324/232 |
| 5,262,722 | 11/1993 | Hedengren et al. .................... | 324/242 |
| 5,315,234 | 5/1994 | Sutton, Jr. et al. ..................... | 324/242 |
| 5,345,514 | 9/1994 | Mahdavich et al. ...................... | 382/8 |
| 5,371,461 | 12/1994 | Hedengren .............................. | 324/225 |
| 5,371,462 | 12/1994 | Hedengren et al. .................... | 324/225 |
| 5,389,876 | 2/1995 | Hedengren et al. .................... | 324/242 |
| 5,418,457 | 5/1995 | Hedengren et al. .................... | 324/225 |

FOREIGN PATENT DOCUMENTS

| | | |
|---|---|---|
| 2853457A1 | 12/1978 | (DE) . |
| 0439912A2 | 11/1990 | (EP) . |
| 0439912A3 | 11/1990 | (EP) . |

\* cited by examiner

*Primary Examiner*—Gerard R. Strecker
(74) *Attorney, Agent, or Firm*—David C. Goldman; Jill M. Breedlove

(57) ABSTRACT

The invention provides a system and method for normalizing and calibrating a sensor array. The sensor array can comprise differential element sensors, such as for example eddy current sensors, or absolute sensors. A single test specimen is used to normalize and calibrate the sensor array using one or more scans of the test specimen. Notably, only one alignment of the sensor array to the test specimen is required. The test specimen is preferably made of the same or similar type of material as the part to be tested and is of a similar geometric shape that can have a simple flat surface or a more complex surface. A linear feature and several notches are machined into the surface of the specimen by using, for example, electro-discharge machining methods, to provide the necessary signals when scanned by the sensor array. Signals from the linear feature on the test specimen are used to remove any bias and to normalize the dynamic ranges of all of the sensors in the array. Signals from the notches are used to establish the gain settings for the sensors in the array.

18 Claims, 4 Drawing Sheets

SYSTEM AND METHOD FOR NORMALIZING AND CALIBRATING A SENSOR ARRAY

CROSS REFERENCE TO RELATED APPLICATIONS

This application claims priority under 35 U.S.C. Section 119 to prior U.S. Provisional Application Serial No. 60/090,293, filed Jun. 23,1998.

BACKGROUND OF THE INVENTION

The present invention relates generally to sensor arrays and more particularly to normalizing and calibrating a sensor array.

An array of sensors can be used to detect and/or measure the dimension of defects in metal components and parts. In this regard, each sensor in the array is capable of producing an electrical signal indicative of a defect in a metal component or part. Multiple sensors can be used together as an array to scan an area of the component or part that is larger than if a single sensor was used. However, in order to accurately detect and/or measure the defect, it is important that all of the sensors in the array react in the same way (i.e., produce the same electrical signal) to the same defect. For this to occur, the sensors in the array should all have the same dynamic range and respond identically in signal amplitude to the same defect.

To obtain uniform reaction from sensors, the sensors are normalized and calibrated. For example, flexible eddy current array sensors used to inspect aircraft engine components have been previously normalized and calibrated using two separate specimens, one to normalize the signal from all sensor elements and the other to calibrate the element signal level. For normalization, all elements are scanned across a linear feature. A correction factor and offset is calculated for each element from its signal level and saved for use during later testing of a part. For calibration, one of the sensor elements is used to scan a single notch on a test specimen in two dimensions. This process can be time consuming because a significant amount of time is required to properly align the sensor array to each test specimen. In this regard, the sensor needs to be aligned with the test specimen at minimum two times. Furthermore, the two-dimensional scan is done at a high spatial resolution. Moreover, the result's accuracy is limited because the data are obtained using a test specimen that may not match the geometric shape of the part to be inspected so the part test conditions may not match the calibration conditions. Thus, the data may not sufficiently represent the scanning conditions of a sensor array used to scan components or parts having complex surfaces.

SUMMARY OF THE INVENTION

Thus, there is a need for a faster, simpler, and more accurate system and method to normalize and calibrate sensor arrays. The present invention is a system, test specimen and method for normalizing and calibrating an array of sensors using one or more scans of a single test specimen. Notably, only one alignment of the sensor to the test specimen is required. The test specimen is preferably made of the same or similar type of material and is of a similar geometric shape (e.g., a simple flat surface or a more complex surface) as the metal component or part to be scanned for defects. The test specimen further comprises at least one linear feature and multiple notches that are machined into the surface of the test specimen. Both the linear feature and the notches cause the sensors in the array to produce electrical signals that are used to normalize and calibrate the sensor arrays. The method uses the electrical signal trace produced by each sensor in the array and caused by the respective sensor detecting the linear feature on the test specimen during scanning to remove any bias and to normalize the dynamic range of each sensor in the array. The method further uses the electrical signal trace produced by particular sensors in the array and caused by the respective sensor detecting one or more of the multiple notches of the test specimen during scanning to establish the gain settings for and calibrate each sensor in the sensor array.

DETAILED DESCRIPTION OF THE INVENTION

Figure 1:
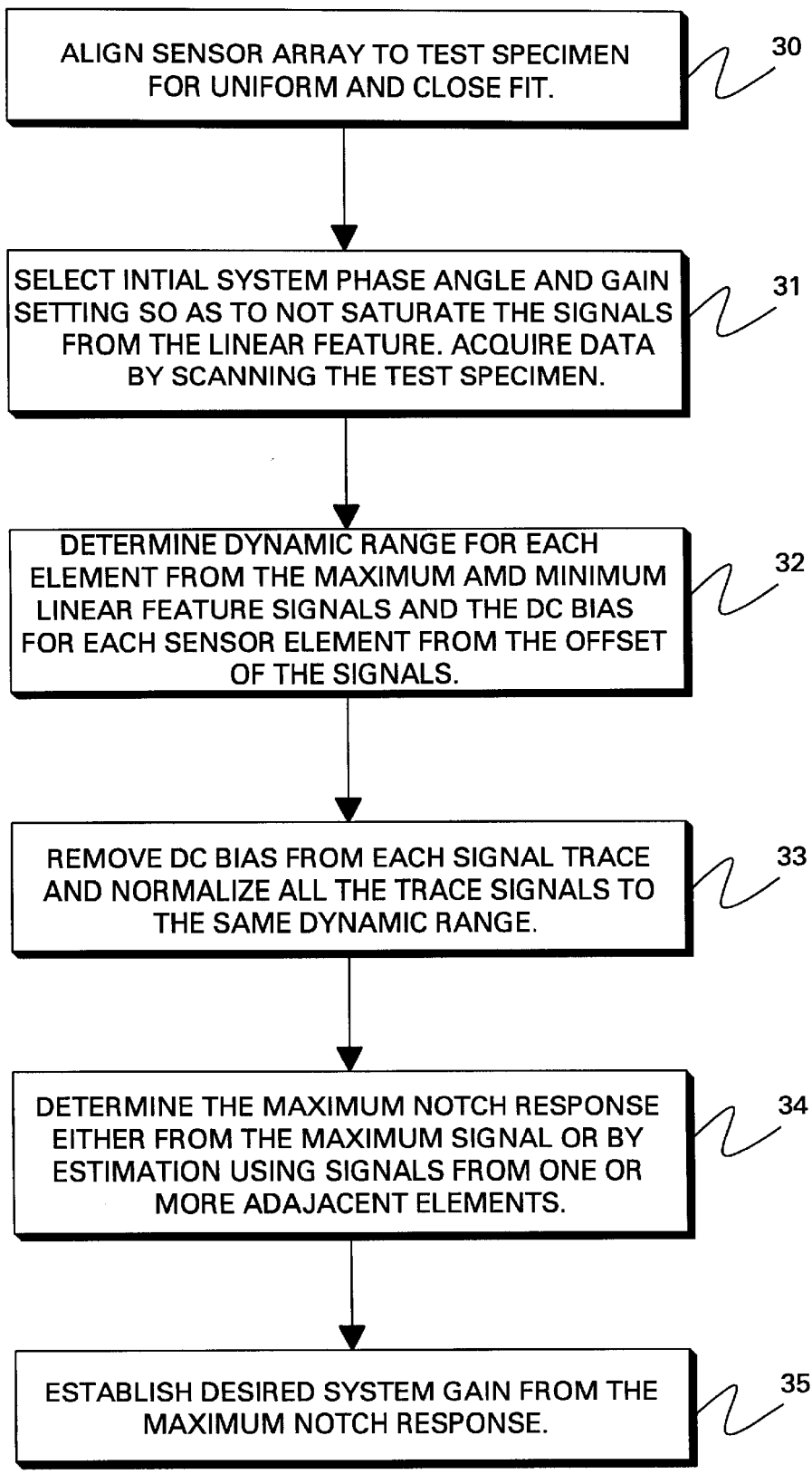
FIG. 1 shows a flow chart setting forth the steps for calibrating and normalizing an array of eddy current sensors according to one embodiment of this invention.
Figure 2:
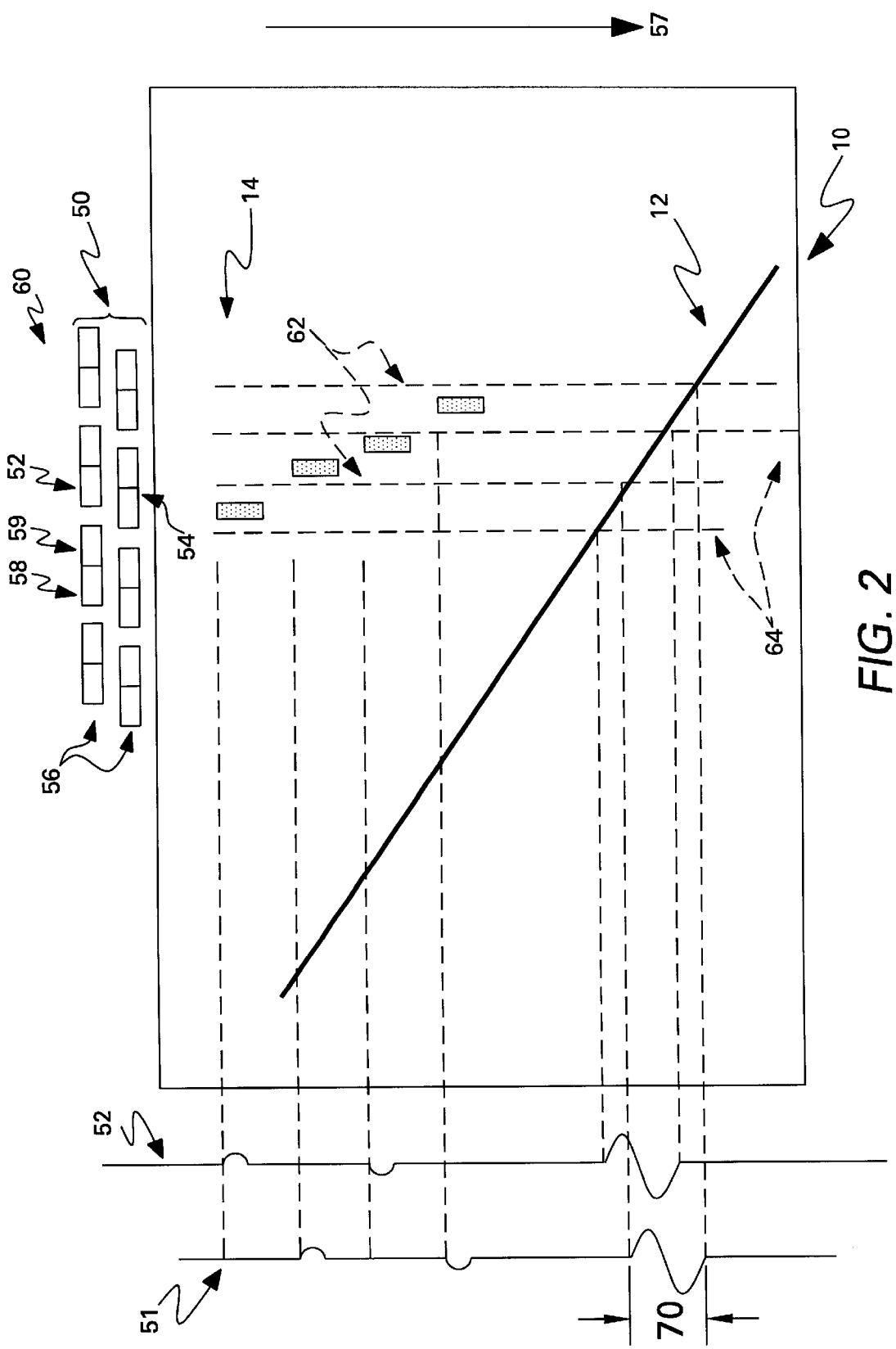
FIG. 2 shows a top view of a test specimen having a flat surface according to this invention.
Figure 4:
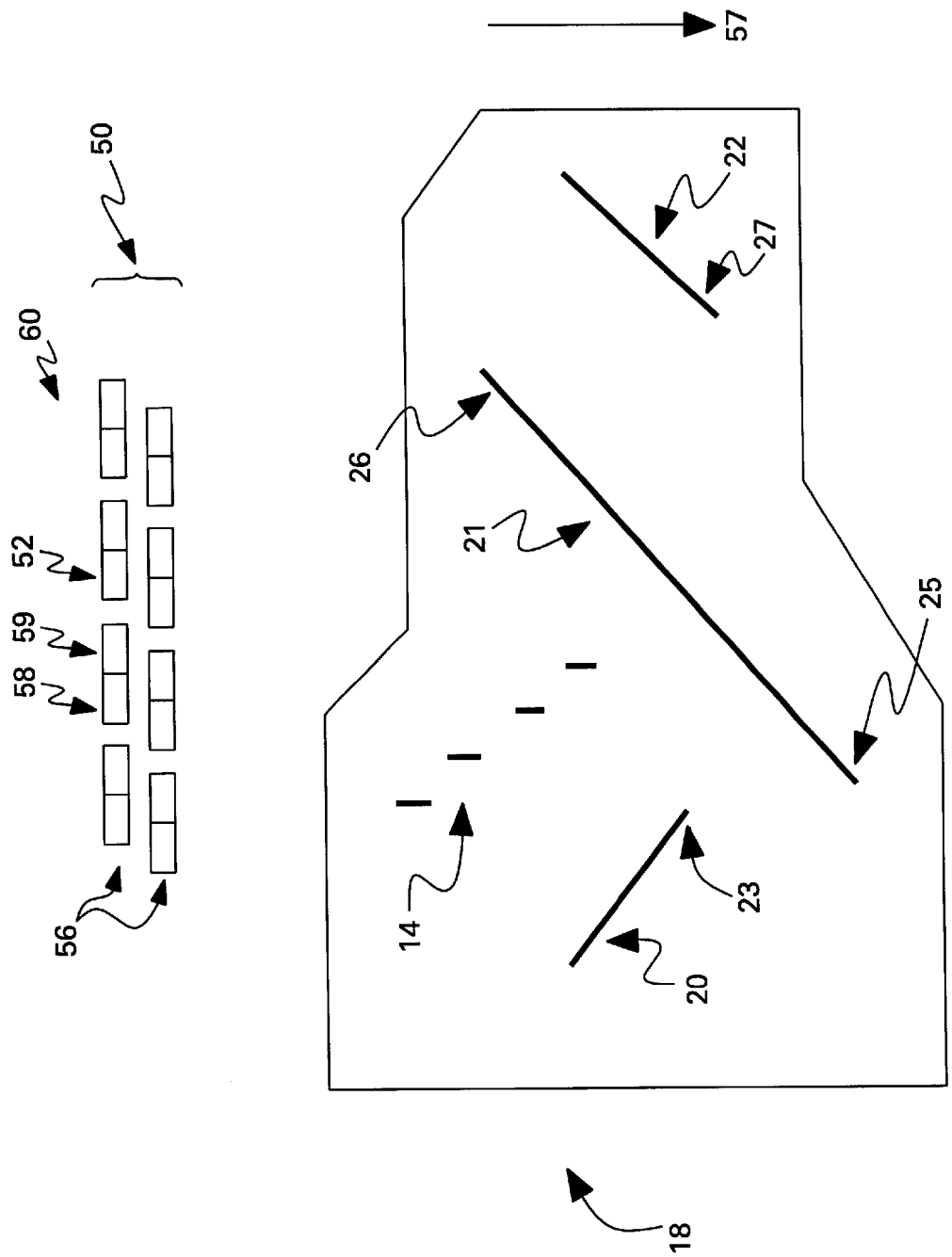
FIG. 4 shows a top view of the test specimen shown in FIG. 3 with the interior surface of the test specimen flattened in two dimensions.

FIG. 1 shows a flow chart that sets forth the steps for calibrating and normalizing an array 50 of eddy current sensors 60 shown in FIGS. 2 and 4 according to one embodiment of the present invention. Each of the eddy current sensors 60 comprise a pair of differentially-connected elements 58, 59, i.e., dual coils. It should be noted, however, that the present invention is equally applicable to sensors comprising absolute-type elements, i.e., single coils.

Figure 3:
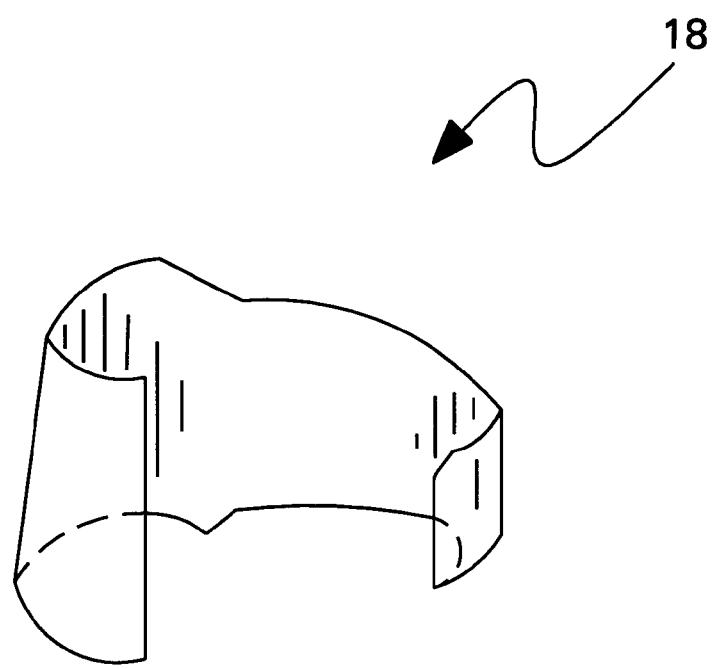
FIG. 3 shows a perspective view of a test specimen having a complex surface.

Initially, a test specimen is selected. The test specimen will be scanned by the sensor array 50 that is to be normalized and calibrated. The test specimen preferably comprises the same or similar material and is of a similar geometric surface shape as the metal component or part to be scanned for defects. In some instances, to simplify fabrication, the test specimen can comprise multiple pieces of material adhered together. FIG. 2 shows a top view of a test specimen 10 having a flat surface. FIG. 3 shows a perspective view of a test specimen 18 having a complex surface. FIG. 4 shows a top view of the test specimen 18 with the interior surface of the test specimen 18 flattened out in two dimensions.

The test specimens comprise at least one linear feature and multiple notches 14 that are machined into the surface of the test specimen, using for example known electro-discharge machining methods. For some applications, the linear feature has a narrow width of about 0.003 inches (three mils) and is sufficiently deep to be considered infinitely deep by the differential elements of the sensors 60 (i.e., the signal amplitude does not increase if the notch 14 is even deeper), although these measurements may vary according to the application. For all applications, the length of the linear feature or combination of linear features should cover the scanning area of the sensor array 50 such that all of the sensors 60 produce a signal as a result of detecting the linear feature. For some applications, the notches 14 are about fifteen mils deep by about thirty mils long by about three mils (0.015"×0.030"×0.003"), although these measurements may vary according to the application. For all applications, the notches 14 should be positioned in the direction of the scanning in such a way that an element can only pass over one notch at the same time. The notches should be separated by about ¾ of the element's width in the horizontal direction, though other separations may also be used. Referring to FIG. 2, the test specimen 10 comprises a linear feature 12 and notches 14. Referring to FIG. 4, the test specimen 18 comprises multiple linear feature s 20, 21 and 22 and notches 14.

Next, the eddy current sensor array 50, which is shown in FIGS. 2 and 4 having two staggered rows 56 of sensors 60, is aligned to the previously selected test specimen at 30. Referring to FIG. 2, the sensor array 50 is aligned to the test specimen such that (i) the linear feature covers the scanning area of the sensor array 50; and (ii) only one sensor 54 from the first row of the sensor array 50 and only one sensor 52 from the second row of the sensor array 50 pass over the notches 14. Notably, only one alignment of the sensor array 50 to the test specimen is necessary.

Next, an initial system phase angle and gain setting are selected, and a scan of the test specimen is made at 31. The scan of the test specimen is taken in the direction 57. The phase angle and gain setting are selected such that the electrical signals produced by the sensors 60 are not saturated when the sensor array 50 is used to scan the test specimen. For example, the phase angle and gain setting can be selected using data obtained from prior experience using the sensor array 50. Alternatively, the phase angle may be selected to optimize electrical signal amplitude in only one channel. The selected phase angle and gain setting produce a set of traces, one from each sensor 60 in the array 50 when a scan of the test specimen is taken. By way of example, a trace 51 for sensor 52 and trace 53 for sensor 54 are shown in FIG. 2. The scanning path 62 for sensor 52 and the scanning path 64 for sensor 54 are also shown in FIG. 2.

Next, a dynamic range for each sensor in the array 50 is determined at 32 from the maximum and minimum amplitude of the electrical signals produced by each sensor 60 in the array 50 as a result of detecting the linear feature. The dynamic range is a reflection of sensor to surface fit and of sensor element fabrication accuracy. The DC bias for each sensor 60 is also determined at 32 from the offset of the electrical signals produced by each sensor 60 in the array 50. Referring to FIG. 2, the test specimen 10 comprises the linear feature 12 which spans an area wider than the inspection width of the array of sensors 50, and is slanted relative to the scanning direction 56 of the sensor array 50. The linear feature 12 enables the differential components of each sensor 60 to be normalized using the electrical signals produced by each sensor in the array 50. As a result, the electrical signals produced comprise both maximum and minimum amplitude, as shown by the traces in FIG. 2. The width 70 of the signal produced relates to the width of the differential element (coils 58 and 59) and the angle of the linear feature with respect to the element. It should be noted that the linear feature 12 is not perpendicular to the scanning direction of the sensor array 50. If the linear feature 12 were positioned perpendicular to the scanning direction of the sensor array 50, it would not be possible to normalize the array of sensors 50 because the electrical signals produced by the differential elements 58, 59 of each sensor 60 would cancel each other as the sensor 60 passed over the linear feature 12. If the array of sensors comprise sensors having absolute elements, the linear feature may be positioned perpendicular to the scanning direction of the sensor array.

FIG. 4 shows a test specimen 18 comprising a first linear feature 20, a second linear feature 21, and a third linear feature 22, to allow for a more accurate measurement of the dynamic range and DC bias in metal components and parts having complex surfaces. In this regard, it may be difficult to fabricate a single linear feature into a part with a complex surface geometry. Consequently, multiple overlapping segments of linear features may be fabricated to provide the same function of a single linear feature. The multiple linear features cover the complete inspection width of the sensor array 50. Referencing FIG. 3, the first linear feature 20 is positioned such that the end 23 of the first linear feature 20 overlaps with the end 25 of the second linear feature 21, and the end 26 of the second linear feature 21 overlaps with the end 27 of the third linear feature 22. The overlap compensates for spatial differences between the sensor elements 58, 59 and the portion of the surface of the test specimen 18 being scanned. Next, the DC bias is removed from each signal trace and all of the trace signals are normalized to the same dynamic range at 33.

Next, the maximum signal produced by a sensor 60 as a result of detecting a notch 14 is calculated from the notch signals at 34 by choosing either the maximum signal or by using some signal combination from sensors 60 that are adjacent overlapping elements in the two staggered rows that both pass over the notch 14 to sensors 52, 54 to approximate the maximum response. Referring to FIGS. 2 and 4, the test specimens 10, 18 comprise multiple notches 14, which are perpendicularly oriented to the array of sensors 50 and offset from each other such that the ends of the notches do not overlap. The number of notches 14 and the horizontal offsets between the notches 14 are determined based on the geometry and spatial response function of a typical sensor 60 to ensure that a peak response can be calculated from the acquired data. The more uniform the sensor's 60 response along the width of the sensor 60, the fewer notches that are needed. As shown in FIGS. 2 and 4, the array of sensors 50 comprises two staggered rows of eddy current sensors 60. As specifically shown in FIG. 2, the notches 14 are positioned on the test specimen 10 such that the notches 14 fall into the scanning path of only one sensor from the first row of sensors and only one sensor from the second row of sensors. By way of example, a trace 51 for sensor 52 and trace 53 for sensor 54 are shown in FIG. 2. The scanning path 62 for sensor 52 and the scanning path 64 for sensor 54 are also shown in FIG. 2. Similarly, in FIG. 4, the notches 14 are positioned on the test specimen 18 such that the notches 14 fall into the scanning path of only one sensor from the first row of sensors and only one sensor from the second row of sensors. As a consequence, the electrical signal produced by the sensors 52, 54 are used to establish the system gain.

The electrical signals produced by the sensors 52, 54 as a result of detecting the notches 14 are next used to improve the maximum signal estimate, and the required system gain is then established from the maximum signal estimate at 35. If the gain for the sensors 60 that was used to normalize is not high enough to give satisfactory signals from the sensors 60 for the notches 14, then a second scan may be taken at a higher system gain (which now may result in saturated signals from the linear feature) to better evaluate the signals produced as result of sensors 52, 54 detecting the notches 14. Lower notch signal amplitudes using a single scan may result in the need for enhancement type signal processing to analyze the notch responses, but with two scans this should not be required. The normalization/calibration process is then completed and the sensor array 50 can be used for testing parts with appropriate settings, as determined by the normalization/calibration process, for reliable defect detection or other measurements.

Additional scans may be taken to determine optimum phase angles for one or both of the linear feature and the notches. Alternatively, the phase angle may be known a priori for a given system/sensor combination and used directly. The order of the normalization and calibration steps may be interchanged if the test specimen is a simple, flat surface. However, if the surface is complex, the sensor array 50 may not conform identically across the surface of the test specimen and the normalization step should preferably be done first to produce best results.

The foregoing has been described for eddy current array sensors, but a similar normalization/calibration method can also be applied to other array sensors (e.g., thermocouple, ultrasound or digital x-ray arrays). In addition, different algorithms for analyzing and/or combining the data can be developed within the scope of this invention. Variations on the test specimen design for dual-use is also within the scope of this invention.

It is therefore apparent that there has been provided in accordance with the present invention, a system, test specimen and method for normalizing and calibrating an eddy current sensor array that fully satisfy the aims and advantages and objectives set forth herein. The invention has been described with reference to several embodiments, however, it will be appreciated that variations and modifications can be effected by a person of ordinary skill in the art without departing from the scope of the invention.

What is claimed is:

1. A method for simultaneously normalizing and calibrating a sensor array, the sensor array for use in scanning a work piece to detect discontinuities in the work piece, said method comprising the steps of:

providing a sensor array having multiple sensors capable of producing an electrical signal indicative of a discontinuity in a work piece;

providing a test specimen comprising at least one linear feature and at least two notches;

scanning said test specimen using said sensor array to produce multiple electrical signal traces indicative of said linear feature and said at least two notches; and using said multiple electrical signal traces to adjust each said sensors of said sensor array to obtain uniform electrical signal from each said sensor.

2. The method of claim 1, further comprising the step of: aligning said sensor array to said test specimen.

3. The method of claim 2, wherein said sensor array comprises two staggered rows of sensors;

wherein said step of aligning said array of sensors to said test specimen further comprises:

aligning said sensors with said linear feature such that said linear feature covers the scanning area of said sensor array;

aligning a first sensor from said first row of said sensor array such that said first sensor passes over said notches during scanning; and aligning a second sensor from said second row of said sensor array such that said second sensor passes over said notches during scanning.

4. The method of claim 1, wherein said sensor array comprises eddy current sensors.

5. The method of claim 1, wherein said sensor array comprises sensors comprising absolute elements.

6. The method of claim 1, wherein said test specimen comprises the substantially same material as the work piece.

7. The method of claim 1, wherein said linear feature is slanted relative to the scanning direction of the sensor array.

8. The method of claim 1, wherein said linear feature is perpendicular relative to the scanning direction of the sensor array.

9. The method of claim 1, wherein said step of using the multiple electrical signal traces to adjust each said sensor of said sensor array to obtain uniform electrical signal from each said sensor further comprises the step of:

normalizing said sensor array using the electrical signals produced by said sensors as a result of detecting said linear feature.

10. The method of claim 1, wherein said step of using the multiple electrical signal traces to adjust each said sensor of said sensor array to obtain uniform electrical signal from each said sensor further comprises the step of:

calibrating said sensor array using the electrical signals produced by said sensors as a result of detecting said at least two notches.

11. The method of claim 1, wherein said step of using the multiple electrical signal traces to adjust each said sensor of said sensor array to obtain uniform electrical signal from each said sensor further comprises the step of:

determining the dynamic range for each said sensor in said sensor array from the maximum and minimum electrical signals produced by each sensor as a result of detecting said linear feature.

12. The method of claim 11, further comprising the step of:

using the dynamic range determined to normalize the electrical signals produced by each said sensor.

13. The method of claim 1, wherein said step of using the multiple electrical signal traces to adjust each said sensor of said sensor array to obtain uniform electrical signal from each said sensor further comprises the step of:

determining the DC bias for each said sensor from the offset of the electrical signals produced by each said sensor as a result of detecting said linear feature.

14. The method of claim 13, further comprising the step of:

removing the DC bias from each electrical signal produced by each said sensor as a result of detecting the linear feature.

15. The method of claim 1, wherein said step of using the multiple electrical signal traces to adjust each said sensor of said sensor array to obtain uniform electrical signal from each said sensor further comprises the step of:

determining the maximum notch response from the maximum electrical signals produced by each said sensor as a result of detecting said at least two notches.

16. The method of claim 15, further comprising the step of:

establishing the desired system gain from the maximum notch response.

17. The method of claim 1, wherein said step of using the multiple electrical signal traces to adjust each said sensor of said sensor array to obtain uniform electrical signal from each said sensor further comprises the step of:

determining the maximum notch response from estimation using signals produced by said sensors adjacent to said sensors detecting said at least two notches.

18. A system for simultaneously normalizing and calibrating a sensor array, the sensor array for use in scanning a work piece to detect discontinuities in the work piece, said system comprising:

a sensor array having multiple sensors capable of producing an electrical signal indicative of a discontinuity in a work piece;

a test specimen comprising at least one linear feature and at least two notches;

wherein said test specimen is scanned using said array to produce multiple electrical signal traces indicative of said linear feature and said at least two notches; and wherein said multiple electrical signal traces are used to adjust each said sensor of said sensor array to obtain uniform electrical signal from each said sensor by normalizing the sensor array using the electrical signals produced by the sensor array as a result of detecting said linear feature and calibrating the sensor array using the electrical signals produced by the sensor array as a result of detecting said at least two notches.

* * * * *